(12) United States Patent
Avinash et al.

(10) Patent No.: US 8,761,479 B2
(45) Date of Patent: Jun. 24, 2014

(54) SYSTEM AND METHOD FOR ANALYZING AND VISUALIZING SPECTRAL CT DATA

(75) Inventors: Gopal Biligeri Avinash, Menomonee Falls, WI (US); Sandeep Dutta, Waukesha, WI (US); Saad Ahmed Sirohey, Pewaukee, WI (US); Ananth P. Mohan, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 898 days.

(21) Appl. No.: 12/941,162

(22) Filed: Nov. 8, 2010

(65) Prior Publication Data

US 2012/0114206 A1 May 10, 2012

(51) Int. Cl.
*G06K 9/00* (2006.01)

(52) U.S. Cl.
USPC ........................................ 382/131

(58) Field of Classification Search
None
See application file for complete search history.

(56) References Cited

U.S. PATENT DOCUMENTS

| | | | | |
|---|---|---|---|---|
| 7,634,044 | B2* | 12/2009 | Bruder | 378/9 |
| 2002/0109839 | A1* | 8/2002 | Faus et al. | 356/300 |
| 2007/0041490 | A1* | 2/2007 | Jha et al. | 378/8 |
| 2007/0263915 | A1* | 11/2007 | Mashiach | 382/130 |
| 2008/0260094 | A1* | 10/2008 | Carmi | 378/19 |
| 2009/0074150 | A1* | 3/2009 | Jaffray et al. | 378/197 |
| 2009/0138279 | A1 | 5/2009 | Avinash et al. | |
| 2009/0290772 | A1 | 11/2009 | Avinash et al. | |
| 2009/0292478 | A1 | 11/2009 | Avinash et al. | |
| 2009/0292551 | A1* | 11/2009 | Sirohey et al. | 705/2 |
| 2009/0292557 | A1 | 11/2009 | Sirohey et al. | |
| 2010/0069742 | A1* | 3/2010 | Partain et al. | 600/424 |
| 2010/0131885 | A1 | 5/2010 | Licato et al. | |
| 2011/0228906 | A1* | 9/2011 | Jaffray et al. | 378/65 |
| 2012/0001084 | A1* | 1/2012 | Proksa et al. | 250/393 |
| 2012/0051614 | A1* | 3/2012 | Olszewski et al. | 382/128 |
| 2012/0062901 | A1* | 3/2012 | Yoshida et al. | 356/479 |
| 2012/0076377 | A1* | 3/2012 | Dutta et al. | 382/131 |
| 2012/0114206 | A1* | 5/2012 | Avinash et al. | 382/131 |
| 2012/0123253 | A1* | 5/2012 | Renisch et al. | 600/425 |
| 2012/0294414 | A1* | 11/2012 | Koehler | 378/16 |
| 2013/0004043 | A1* | 1/2013 | Ross et al. | 382/131 |

\* cited by examiner

*Primary Examiner* — Tahmina Ansari
(74) *Attorney, Agent, or Firm* — Ziolkowski Patent Solutions Group, SC (57) ABSTRACT

A system and method for analyzing and visualizing spectral CT data includes access of a set of image data acquired from a patient comprising spectral CT data, identification of a plurality of target regions of interest (TROIs) and a reference region of interest (RROI) from the set of image data, extraction of a plurality of target spectral Hounsfield unit (HU) curves from image data representing the plurality of TROIs, extraction of a reference spectral HU curve from image data representing the RROI, normalization of the plurality of target spectral HU curves with respect to the reference spectral HU curve, and display of the plurality of normalized target spectral HU curves.

26 Claims, 9 Drawing Sheets

SYSTEM AND METHOD FOR ANALYZING AND VISUALIZING SPECTRAL CT DATA

BACKGROUND OF THE INVENTION

Embodiments of the invention relate generally to diagnostic imaging and, more particularly, to a system and method for analyzing and visualizing spectral computed tomography (CT) data.

Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis that ultimately produces an image.

Generally, the x-ray source and the detector assembly are rotated about the gantry within an imaging plane and around the subject. X-ray sources typically include x-ray tubes, which emit the x-ray beam at a focal point. The detector assembly is typically made of a plurality of detector modules. Data representing the intensity of the received x-ray beam at each of the detector elements is collected across a range of gantry angles. The data are ultimately processed to form an image.

Conventional CT systems emit an x-ray with a polychromatic spectrum. The x-ray attenuation of each material in the subject depends on the energy of the emitted x-ray. If CT projection data is acquired at multiple x-ray energy levels or spectra, the data contains additional information about the subject or object being imaged that is not contained within a conventional CT image. For example, spectral CT data can be used to produce a new image with x-ray attenuation coefficients equivalent to a chosen monochromatic energy. Such a monochromatic image includes image data where the intensity values of the voxels are assigned as if a CT image were created by collecting projection data from the subject with a monochromatic x-ray beam.

A principle objective of energy sensitive scanning is to obtain diagnostic CT images that enhance information (contrast separation, material specificity, etc.) within the image by utilizing two or more scans at different chromatic energy states. A number of techniques have been proposed to achieve energy sensitive scanning including acquiring two or more scans either (1) back-to-back sequentially in time where the scans require multiple rotations of the gantry around the subject or (2) interleaved as a function of the rotation angle requiring one rotation around the subject, in which the tube operates at, for instance, 80 kVp and 140 kVp potentials.

High frequency generators have made it possible to switch the kVp potential of the high frequency electromagnetic energy projection source on alternating views. As a result, data for two or more energy sensitive scans may be obtained in a temporally interleaved fashion rather than two separate scans made several seconds apart as typically occurs with previous CT technology. The interleaved projection data may furthermore be registered so that the same path lengths are defined at each energy level using, for example, some form of interpolation.

Spectral CT data facilitates better discrimination of tissues, making it easier to differentiate between materials such as tissues containing calcium and iodine, for example. However, tissue behavior changes depending on a number of variables, such as patient thickness, contrast concentration and injection rate, timing of imaging, and tissue pathology. As such, the range and complexity of data available from spectral CT imaging makes the data difficult for a clinician to easily understand, interpret, discriminate, and make informed decisions. While known systems and methods can be employed to create and display monochromatic images, known systems and methods simply display images created using spectral CT data, and are lacking in regard to user interaction and analysis.

Further, making a diagnosis based on review of an image is a very specialized task and is typically performed by highly-trained medical image experts. However, even such experts can only make a subjective call as to the degree of severity of the disease. Due to this inherent subjectivity, the diagnoses tend to be inconsistent and non-standardized.

Accordingly, in order to use the data in a clinically relevant manner, there is a need for a methodology to compare spectral CT data across patients in a consistent fashion in spite of the above-described unavoidable and uncontrollable variables inherent in spectral CT data.

Therefore, it would be desirable to design a system and method of analyzing and visualizing spectral CT data that overcomes the aforementioned drawbacks.

BRIEF DESCRIPTION OF THE INVENTION

In accordance with one aspect of the invention, a non-transitory computer readable medium has stored thereon a computer program comprising instructions, which, when executed by a computer, cause the computer to access a set of image data acquired from a patient, the set of image data comprising spectral computed tomography (CT) data. The instructions also cause the computer to identify a plurality of target regions of interest (TROIs) from the set of image data, identify a reference region of interest (RROI) from the set of image data, and extract a plurality of target spectral Hounsfield unit (HU) curves from image data representing the plurality of TROIs. Further, instructions cause the computer to extract a reference spectral HU curve from image data representing the RROI, normalize the plurality of target spectral HU curves with respect to the reference spectral HU curve, and display the plurality of normalized target spectral HU curves.

In accordance with another aspect of the invention, a method includes accessing an image dataset comprising spectral CT data acquired from a patient, creating a plurality of TROIs from the image dataset, and extracting a target dataset from the image dataset, the target dataset comprising image data corresponding to the TROIs. The method also includes computing a plurality of target spectral curves from the target dataset, each target spectral curve representing x-ray attenuation for a respective TROI, creating a RROI from the image dataset, and extracting a reference dataset from the image dataset, the reference dataset comprising image data corresponding to the RROI. Further, the method includes computing a reference spectral curve from the reference dataset, normalizing the plurality of target spectral curves with the reference spectral curve, and outputting a visualization of the plurality of normalized target spectral curves.

In accordance with another aspect of the invention, a system for analyzing image data includes a database having stored thereon a patient image dataset acquired from a patient that includes spectral CT data. The system also includes a processor that is programmed to access the image dataset, identify a plurality of TROIs from the patient image dataset, and identify at least one RROI from the patient image dataset. The processor is also programmed to extract spectral CT data for the plurality of TROIs and the RROI from the patient image dataset, generate a plurality of target curves for the plurality of TROIs from the extracted spectral CT data, and generate at least one reference curve for the at least one RROI from the extracted spectral CT data. Further, the processor is programmed to normalize the plurality of target curves with the at least one reference curve, and output the plurality of normalized target curves. The system also includes a graphical user interface (GUI) configured to display the plurality of normalized target curves to a user.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

In addition, certain embodiments of the present invention provide systems, methods, and computer instructions for analyzing multi-energy data, such as dual energy data, for example. Certain multi-energy data can be used in spectral imaging systems, such as photon counting systems, for example. Dual energy data, which is a type of multi-energy data, can be embodied in monochromatic images, material density images, and/or effective-Z images. While many of the embodiments described herein are discussed in connection with dual energy data, the embodiments are not limited to dual energy data and can be used in connection with other types of multi-energy data, as one skilled in the art will appreciate. Also, while many of the embodiments discussed herein discussed describe a region of interest that can be selected in an image, a volume of interest can also be selected in an image, as one skilled in the art will appreciate.

Figure 1:
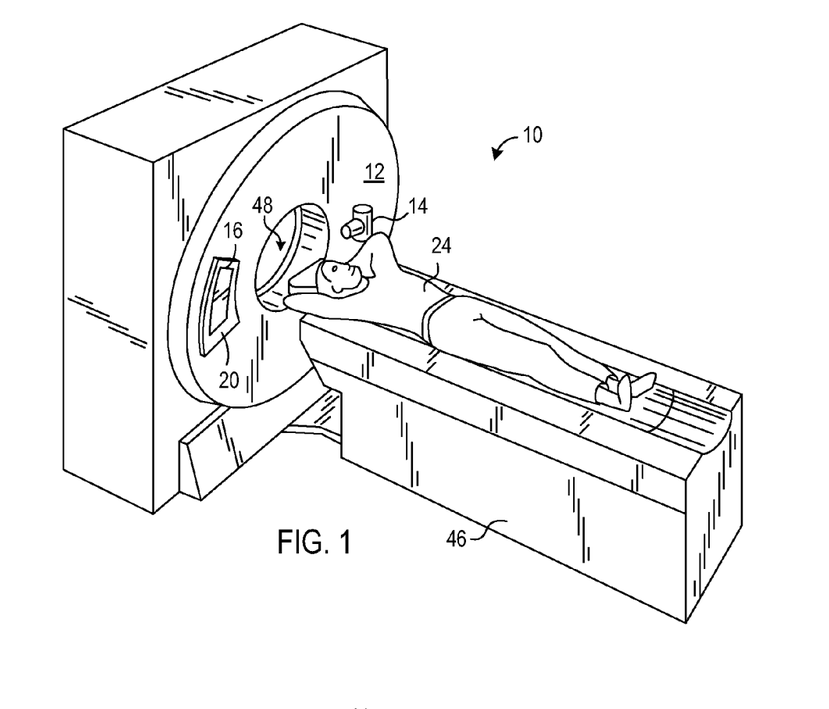
FIG. 1 is a pictorial view of a CT imaging system.
Figure 2:
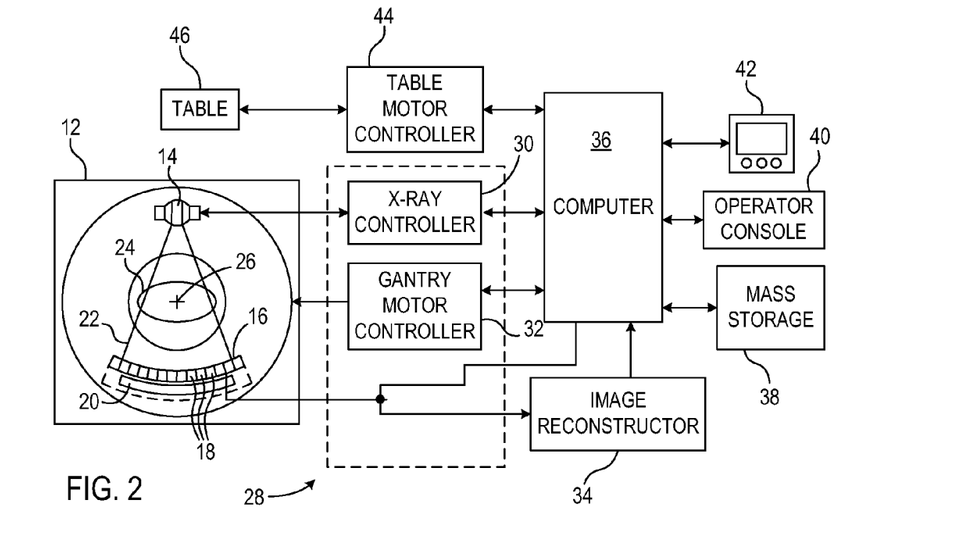
FIG. 2 is a block schematic diagram of the system illustrated in FIG. 1.

Referring to FIG. 1, a CT imaging system 10 is shown as including a gantry 12 representative of a "third generation" CT scanner. Gantry 12 has an x-ray source 14 that projects a beam of x-rays toward a detector assembly or collimator 16 on the opposite side of the gantry 12. Referring now to FIG. 2, detector assembly 16 is formed by a plurality of detectors 18 and data acquisition systems (DAS) 20. The plurality of detectors 18 sense the projected x-rays 22 that pass through a medical patient 24, and DAS 20 converts the data to digital signals for subsequent processing. Each detector 18 produces an analog electrical signal that represents the intensity of an impinging x-ray beam and hence the attenuated beam as it passes through the patient 24. During a scan to acquire x-ray projection data, gantry 12 and the components mounted thereon rotate about a center of rotation 26.

Rotation of gantry 12 and the operation of x-ray source 14 are governed by a control mechanism 28 of CT system 10. Control mechanism 28 includes an x-ray controller 30 that provides power and timing signals to an x-ray source 14 and a gantry motor controller 32 that controls the rotational speed and position of gantry 12. An image reconstructor 34 receives sampled and digitized x-ray data from DAS 20 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 20, x-ray controller 30 and gantry motor controller 32. In addition, computer 36 operates a table motor controller 44 which controls a motorized table 46 to position patient 24 and gantry 12. Particularly, table 46 moves patients 24 through a gantry opening 48 of FIG. 1 in whole or in part.

Figure 3:
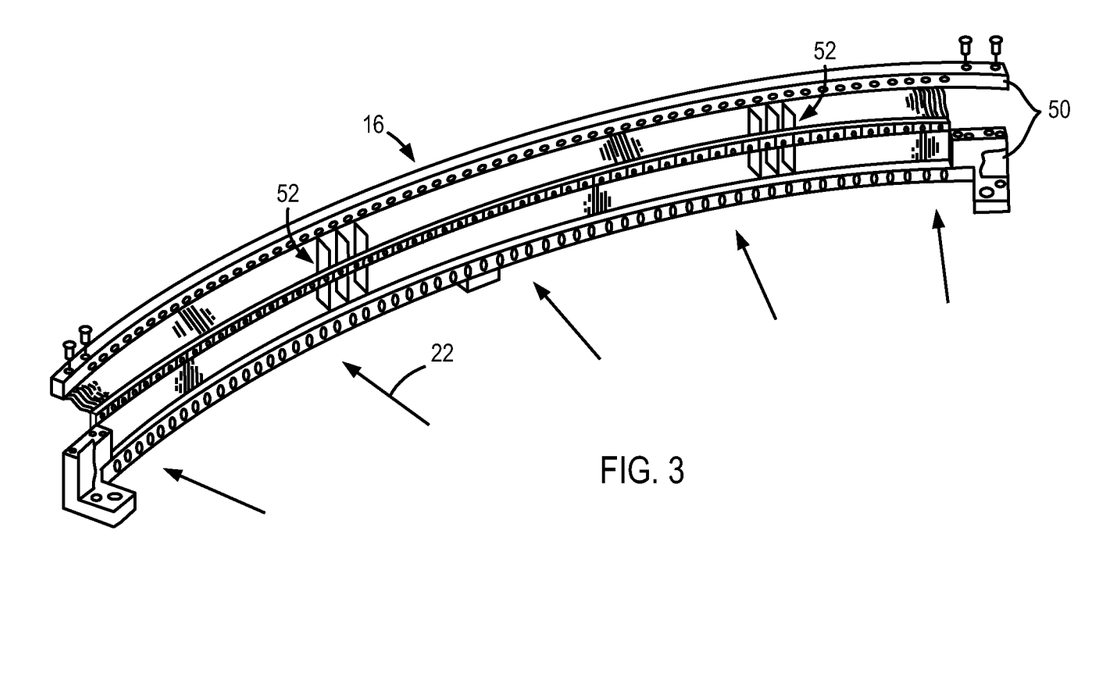
FIG. 3 is a perspective view of one embodiment of a CT system detector array.

As shown in FIG. 3, detector assembly 16 includes rails 50 having collimating blades or plates 52 placed therebetween. Plates 52 are positioned to collimate x-rays 22 before such beams impinge upon, for instance, detector 18 of FIG. 4 positioned on detector assembly 16. In one embodiment, detector assembly 16 includes 57 detectors 18, each detector 18 having an array size of 64×22 of pixel elements 54. As a result, detector assembly 16 has 64 rows and 912 columns (22×57 detectors) which allows 64 simultaneous slices of data to be collected with each rotation of gantry 12.

Figure 4:
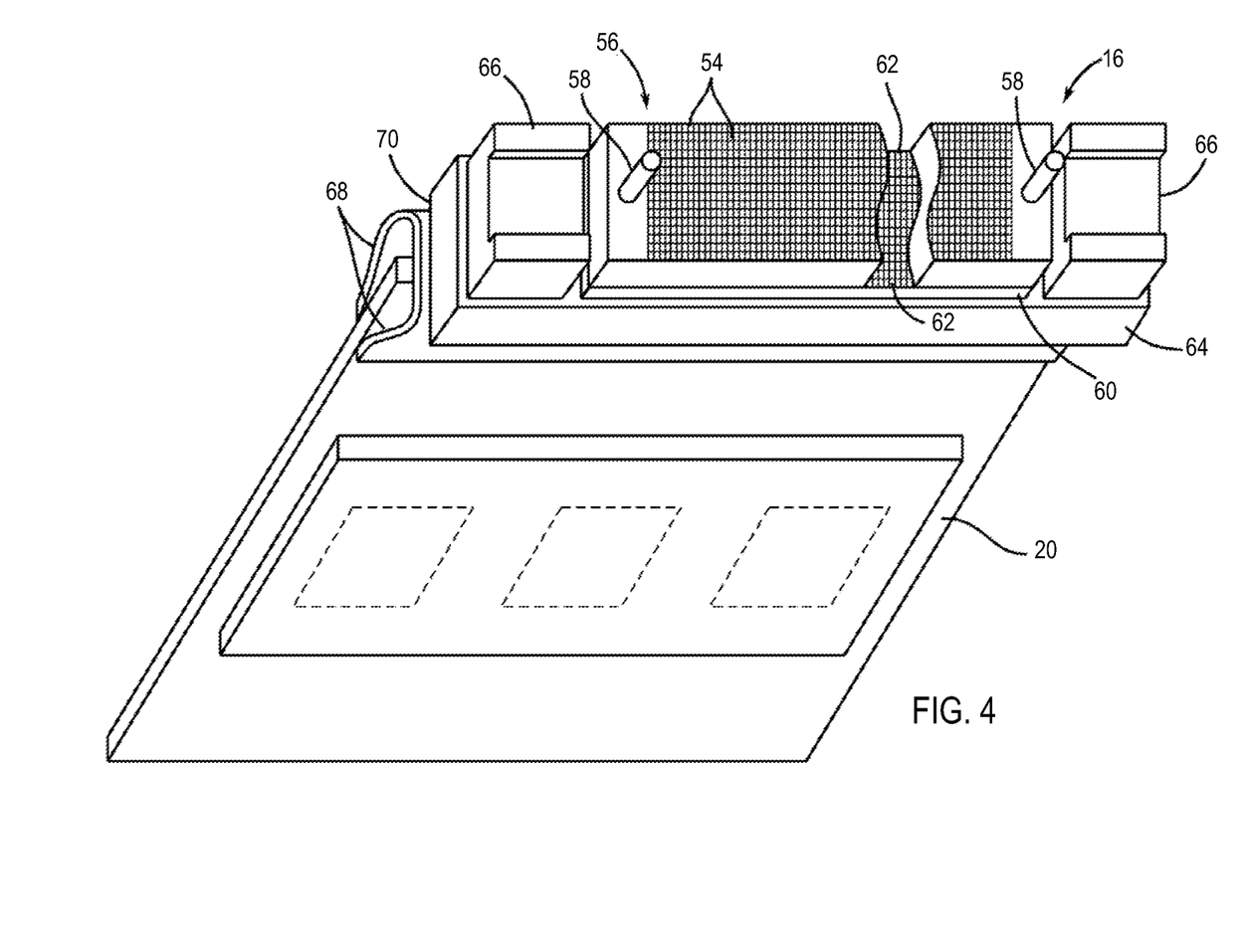
FIG. 4 is a perspective view of one embodiment of a detector.

Referring to FIG. 4, detector 18 includes DAS 20, with each detector 18 including a number of detector elements 54 arranged in pack 56. Detectors 18 include pins 58 positioned within pack 56 relative to detector elements 54. Pack 56 is positioned on a backlit diode array 60 having a plurality of diodes 62. Backlit diode array 60 is in turn positioned on multi-layer substrate 64. Spacers 66 are positioned on multi-layer substrate 64. Detector elements 54 are optically coupled to backlit diode array 60, and backlit diode array 60 is in turn electrically coupled to multi-layer substrate 64. Flex circuits 68 are attached to face 70 of multi-layer substrate 64 and to DAS 20. Detectors 18 are positioned within detector assembly 16 by use of pins 58.

In the operation of one embodiment, x-rays impinging within detector elements 54 generate photons which traverse pack 56, thereby generating an analog signal which is detected on a diode within backlit diode array 60. The analog signal generated is carried through multi-layer substrate 64, through flex circuits 68, to DAS 20 wherein the analog signal is converted to a digital signal.

Figure 5:
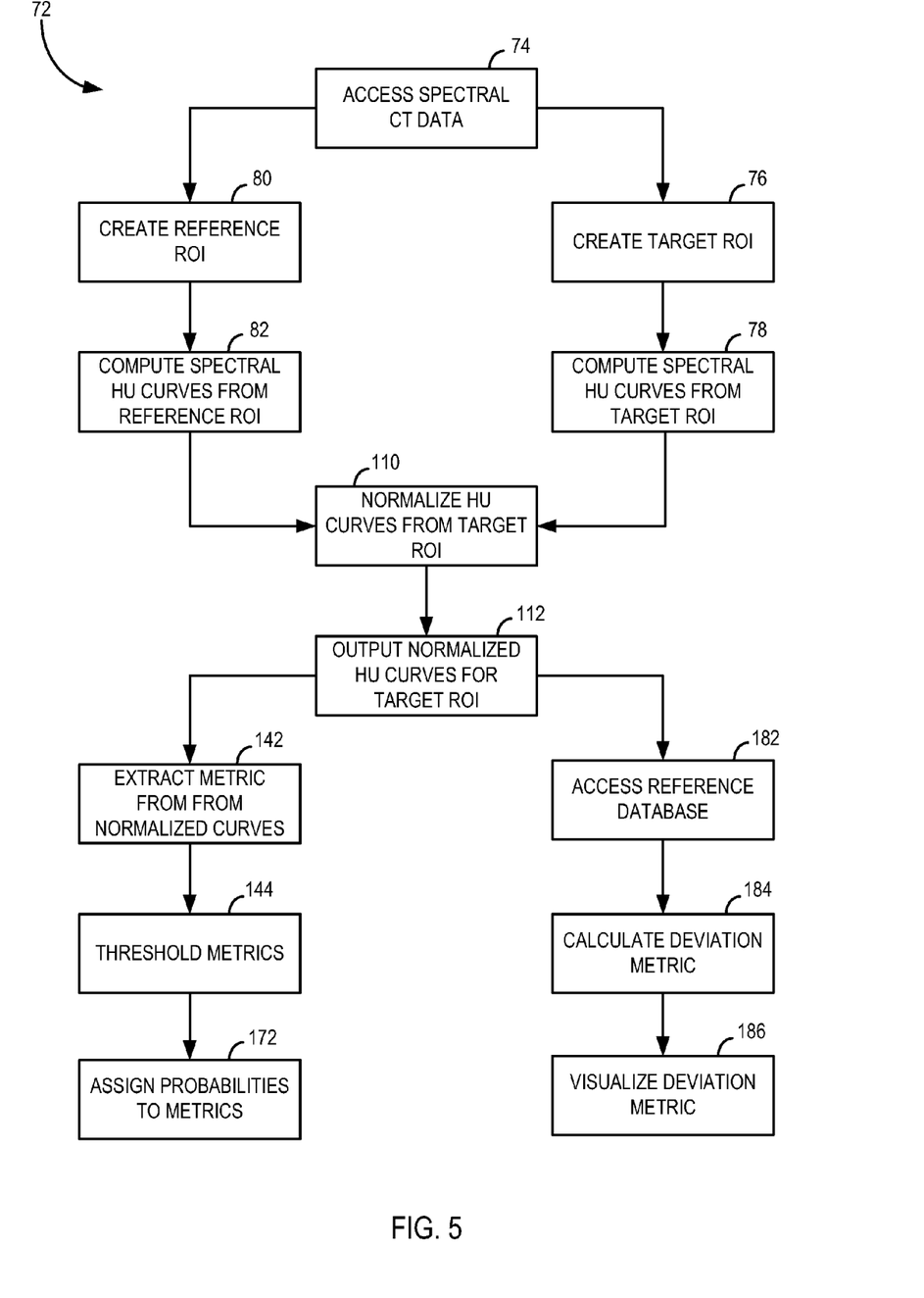
FIG. 5 is a flowchart illustrating a technique for visualization and analysis of spectral CT data in accordance with one embodiment of the present invention.

Referring now to FIG. 5, a technique 72 for analyzing and visualizing spectral CT data is set forth according to an embodiment of the invention. While some embodiments described herein are directed to liver lesion analysis, one skilled in the art will readily recognize that technique 72 may be applied for the analysis of spectral CT data for a range of tissues according to various embodiments, for example, tissue found in the brain, kidneys, liver, etc.

Technique 72 begins at step 74 by accessing a spectral CT dataset acquired from a patient. The spectral CT dataset may be accessed from a storage location or from a live or real-time scan, according to various embodiments. Also, the spectral CT dataset may include image data acquired during a single scan of the patient or during a series of patient scans. At step 76, one or more target regions of interest (TROIs) are selected from the spectral CT dataset. Each TROI may be selected manually, semi-automatically, or automatically according to various embodiments using any combination of available image manipulation tools such as ROI selection, registration, segmentation, contouring, etc. For example, a clinician may select a TROI using an input device on an operator console (e.g., operator console 40 of FIG. 2) by drawing a contour around the TROI in an image of the patient on a display (e.g., display 42 of FIG. 2). As another example, a TROI may be identified using an automated or semi-automated algorithm. In the exemplary liver lesion embodiment, TROIs may correspond to regions including suspected cysts and metastatic tumors.

Spectral Hounsfield Unit (HU) curves are extracted from the spectral CT dataset associated with each TROI at step 78. The HU curves are extracted by calculating HU data at a number of discrete keV levels for each TROI. Various methods may be used to compute the HU data at each keV level. For example, the HU data at each keV level may be calculated as the mean intensity within the respective TROI. One skilled in the art will recognize that numerous alternative methods may be used to compute the HU data.

At step 80, one or more reference regions of interest (RROI) is selected from the spectral CT dataset. The RROI is used to normalize the TROIs under review, as explained in detail below. According to one embodiment, the RROI is selected to represent healthy tissue. As with the TROI, the RROI may be identified manually, semi-automatically, or automatically. Spectral HU curves are extracted from the spectral CT dataset associated with each RROI at step 82 in a similar manner as discussed above with respect to TROIs in step 78.

Figure 6:
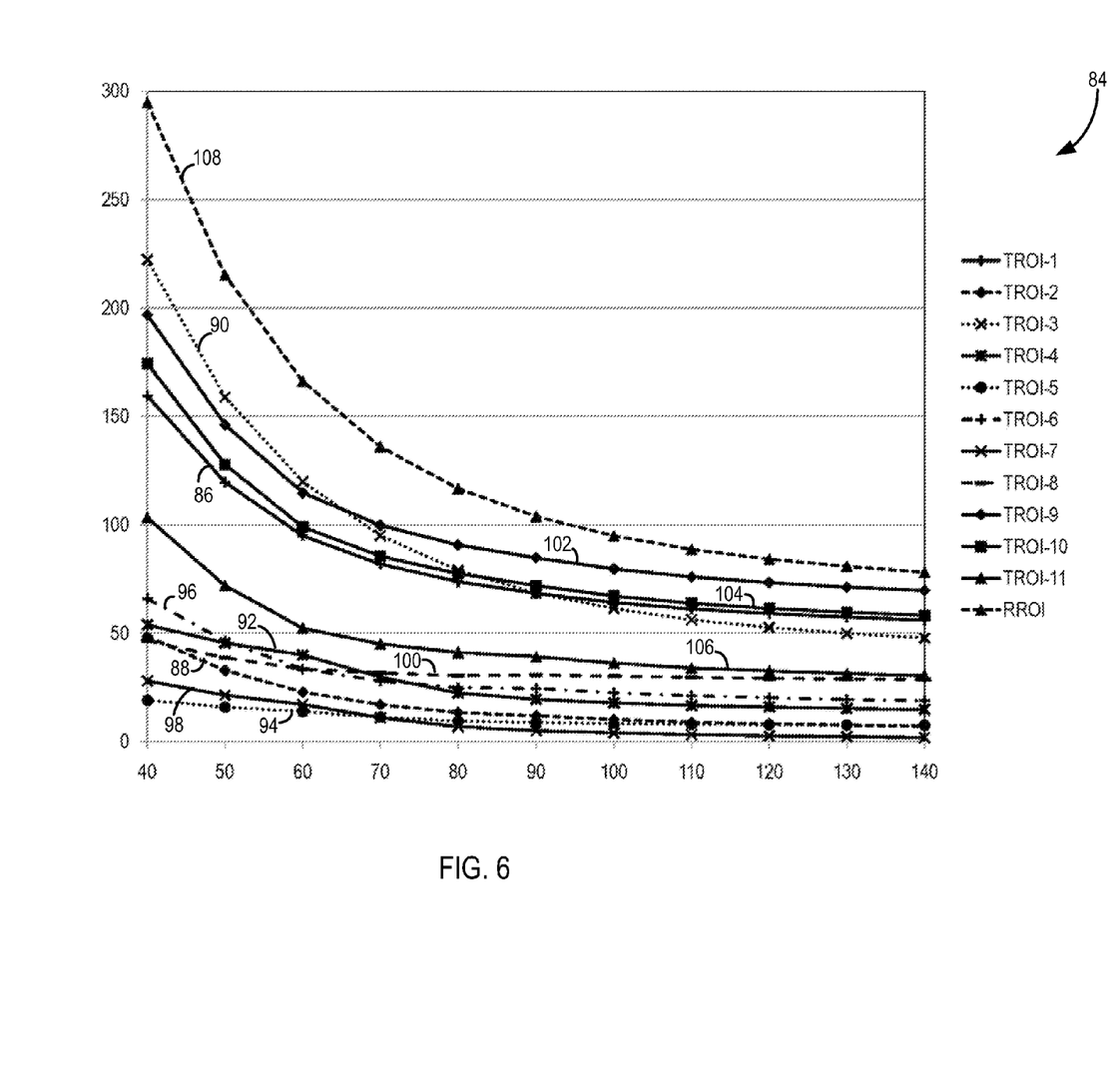
FIG. 6 is a plot of exemplary raw spectral CT data for a number of regions of interest in accordance with one embodiment of the present invention.

Referring now to FIG. 6, an exemplary chart of spectral HU curves 84 is illustrated according to one embodiment. Exemplary TROI curves 86, 88, 90, 92, 94, 96, 98, 100, 102, 104, and 106 correspond to eleven respective TROIs selected from the spectral CT dataset, as described with respect to step 76 of FIG. 4. Exemplary reference ROI curve 108 corresponds to an RROI selected from the spectral CT dataset, such as, for example, liver parenchyma, as described with respect to step 80 of FIG. 5. As shown, the exemplary spectral HU data was calculated for each TROI and RROI at ten discrete keV values over a range of 40 keV to 140 keV. However, one skilled in the art will recognize that any number of discrete keV data points and/or any range of keV values may be used in accordance with embodiments of the invention.

Referring back to FIG. 5, normalized curves for the TROIs are computed at step 110 using the RROI(s). This normalization step adjusts, scales, or otherwise transforms the TROI curves based on the RROI curve in order to facilitate a comparative analysis between the various TROIs. The TROI curves may be normalized using various known methods of normalization. For example, the TROI curves may be divided by the RROI curve by computing the value of the TROI divided by the RROI at each keV level. In an embodiment using multiple RROIs, an average value of the HU data of the RROI curves at each keV level may be used for the division. At step 112, technique 72 outputs the normalized TROI curves.

Figure 7:
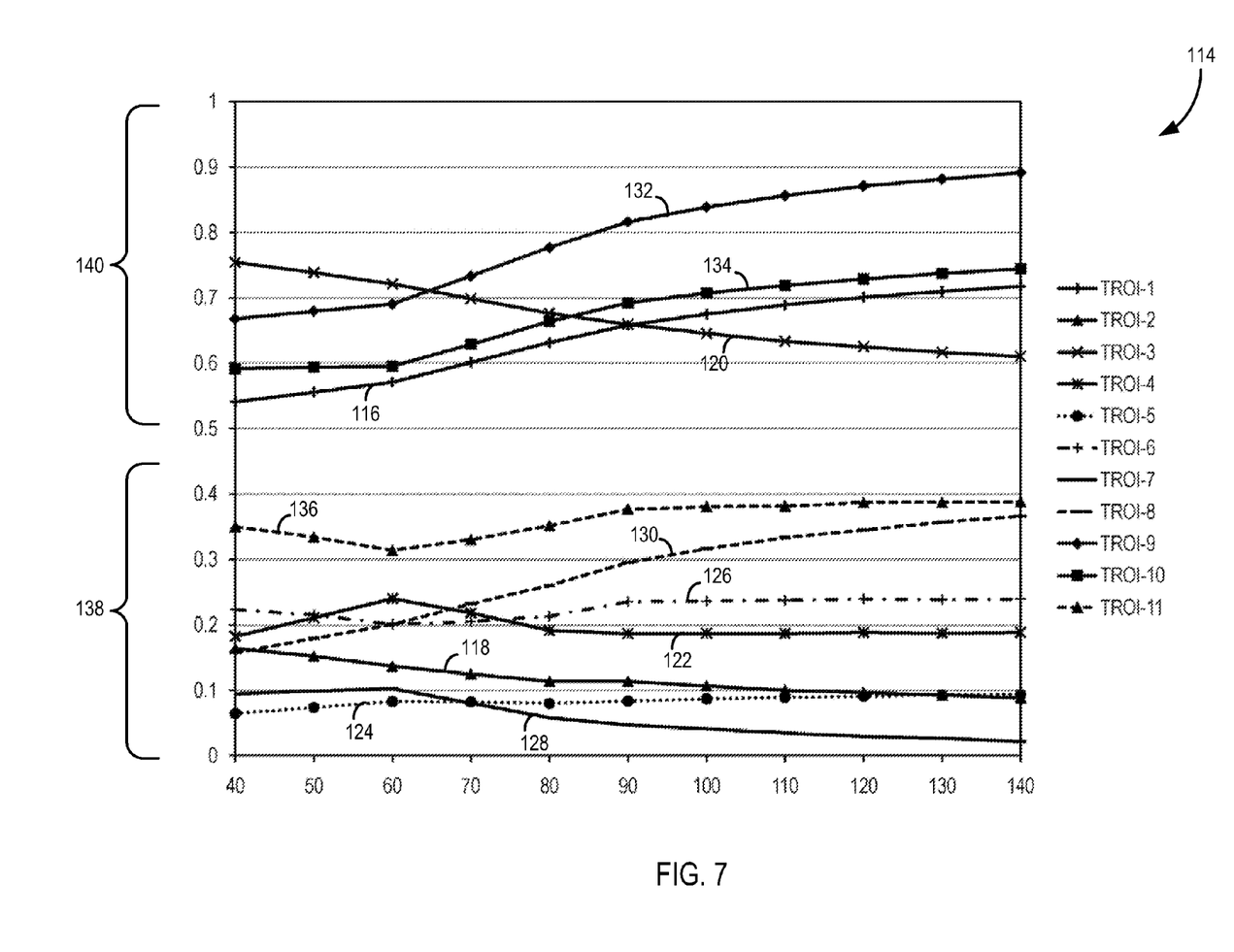
FIG. 7 is a plot of the spectral CT data of FIG. 6 normalized with respect to a reference region of interest in accordance with one embodiment of the present invention.

FIG. 7 provides an exemplary plot 114 of computed normalized TROI curves 116, 118, 120, 122, 124, 126, 128, 130, 132, 134, and 136 for the illustrative liver lesion example. Normalized curves 116-136 represent TROI curves 86-106 of FIG. 6 normalized with respect to RROI curve 108 of FIG. 6. Plot 114 illustrates how normalizing the TROI curves may be used to discriminate between two types of tissue, for example cysts 138 and tumors 140 in the liver. While normalized TROI curves 116-136 are illustrated on a line plot, alternative visual formats may be used to display the TROI curves to a user, including charts, graphs, colors, and the like.

Returning to FIG. 5, technique 72 analyzes the normalized TROI curves at step 142 to derive or extract metrics corresponding to the normalized TROI curves. Numerous methods may be applied to analyze the data. For example, metrics may be extracted from the data via aggregation by summing data across keV levels or performing total area calculations. Alternatively, metrics may be derived using an averaging method, such as, for example, calculating a standard deviation, central tendency, median, or minimum/maximum. As yet another example, metrics may be calculated to represent a rate of decay or change of the normalized TROI curves as a function of keV level.

At step 144, a threshold is applied to the derived metrics to facilitate comparative analysis between the TROIs. The threshold is selected to distinguish between two different tissue types, such as, for example, cysts and metastatic tumors, as described in more detail with respect to FIG. 8. While step 144 of technique 72 is described with respect to a single threshold, it is contemplated that multiple thresholds may be applied to distinguish between any number of distinct tissue types. As such, tissue corresponding to numerous types of tissue may be simultaneously analyzed in a single display.

Figure 8:
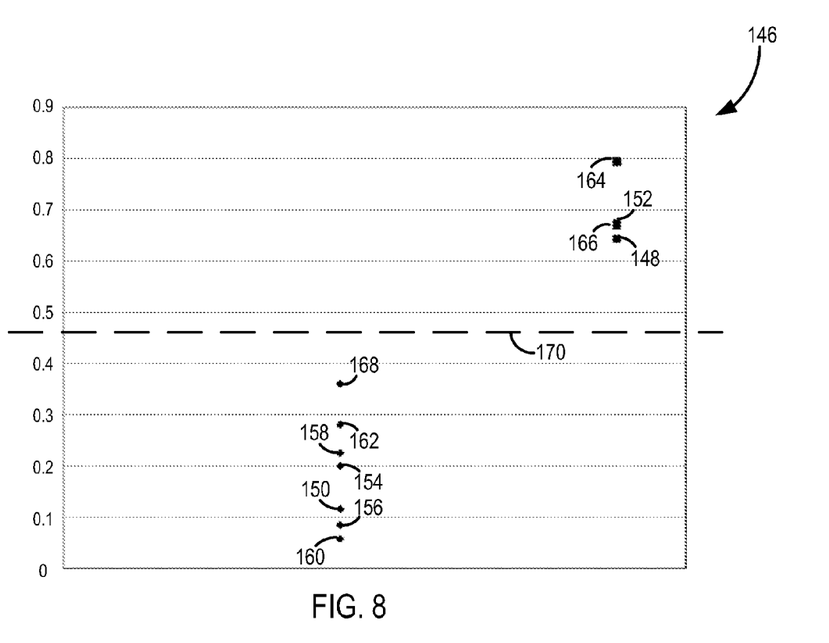
FIG. 8 is a plot of exemplary metrics extracted from the normalized spectral CT data of FIG. 7 in accordance with one embodiment of the present invention.

FIG. 8 is a chart 146 illustrating derived metrics 148, 150, 152, 154, 156, 158, 160, 162, 164, 166, 168 for respective normalized TROI curves 116-136 (FIG. 7) in the liver lesion example. Metrics 148-168 are calculated from the HU data corresponding to TROIs 86-106 (FIG. 6). Metrics 148-168 may be calculated from HU data at all or a subset of the discrete keV levels using any number of techniques, such as, for example, aggregation, averaging, or calculating a rate of decay. In one embodiment, metrics 148-168 are calculated by averaging the HU data at discrete keV levels. As one example, data at two keV levels from each extremity (i.e., 40 and 50 keV and 130 and 140 keV) is ignored. Thus, the metrics are calculated across the 60-120 keV levels. However, the metrics may be calculated from any portion of the HU data. A threshold 170 included in chart 146 greatly facilitates the comparative analysis between metrics 148-168 and is selected to distinguish between two tissue types. As shown, threshold 170 makes it easy to quickly distinguish between TROIs representing cysts (metrics 150, 154-162, and 168) and TROIs representing metastatic tumors (metrics 148, 152, 164, and 166).

FIG. 8 represents an ideal case example, where threshold 170 provides a clear delineation between metrics representing two distinct types of tissue. In some instances, however, an overlap region may occur between metrics representing different tissue types. Nonetheless, an observable difference between the values of the metrics is still exhibited by each tissue type. Thus, referring again to technique 72 of FIG. 5, probabilities may be assigned to the derived metrics at step 172 to facilitate the categorization of metrics that fall within the overlapping zone. As described in detail below with respect to FIG. 9, the probabilities are incorporated into the display of metrics provided to the user, providing "decision-support" assistance of sorts. Once again, any number of distinct tissue types with multiple corresponding thresholds and/or regions of overlap may be simultaneously analyzed in this fashion in a single display.

Figure 9:
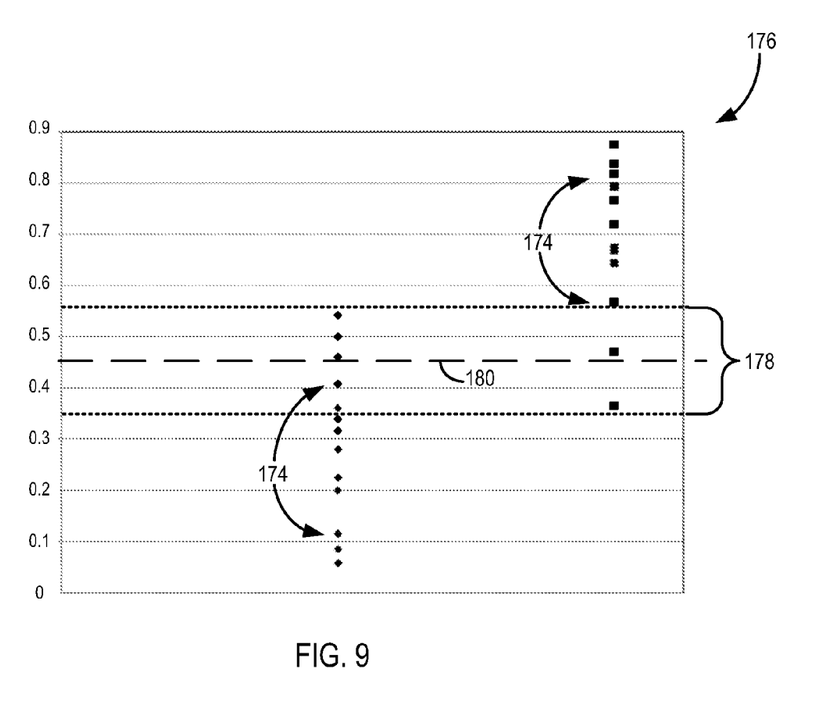
FIG. 9 is a plot of a set of exemplary metrics having an overlap region in accordance with one embodiment of the present invention.

Referring now to FIG. 9, a number of derived metrics 174 calculated from TROI normalized curves are displayed on a chart 176 in a similar manner as described with respect to FIG. 8. Unlike metrics 148-168 of FIG. 8, however, metrics 174 of chart 176 have a distinct region of overlap 178 or confidence interval surrounding a threshold 180. Metrics 174 falling within overlap region 178 may be assigned a probability of corresponding to a particular tissue type using a statistical analysis, such as, for example, a statistical deviation. For example, according to one embodiment, metrics 174 that are within overlap region 178 and are below threshold 180 may be assigned an 80% probability of being a cyst, while metrics 174 that are within overlap region 178 and are above threshold 180 may be assigned an 80% probability of being a metastatic tumor.

The above-described embodiments effectuate tissue categorization of TROIs in a patient by normalizing the TROI data with respect to a reference region defined within the same patient. Reference data may also be used to analyze the quantified spectral CT data for each TROI. Referring back to FIG. 5, a reference database is accessed at step 182. In one embodiment, the reference database contains pre-computed image data acquired from a reference population that represents a pre-defined "expected" tissue behavior. For example, the reference database may include reference data for ROIs containing cysts, may contain data for "normal" or "healthy" tissue, or contain reference data corresponding to a vessel of the patient that is known to have contrast flowing into. Reference image data may be collected from a population of individuals and grouped or standardized according to one or more desired characteristics, such as age, gender, or race.

Comparison between the patient's TROI data and the pre-computed reference data occurs at step 184 through the calculation of a deviation metric. First, the normalized TROI metrics calculated at step 142 are normalized with respect to a set of associated reference metrics calculated from the pre-computed reference data. The normalization accounts for and/or eliminates unavoidable and uncontrollable variables that exist in a given spectral CT dataset. For example, there may be variability in the given spectral CT dataset with respect to the reference database due to a difference in amount of contrast agent used during the scan, the contrast uptake rate may vary between the patient and reference population, and patient size may differ between datasets. Normalization accounts for this variability.

After the patient metrics and reference metrics are normalized, deviation metrics are calculated to represent the deviation between the normalized TROI metrics and the reference metrics. Numerous techniques may be applied to calculate the deviation of the TROI metrics with respect to the pre-computed reference data. In one embodiment, the deviation is defined by a z-score generally corresponding to the number of standard deviations in the difference between the patient TROI metric and the average value of the reference population for a given tissue type.

At step 186 the deviation metrics are displayed to a user. Numerous methods exist to display the actual deviation metrics in a meaningful manner to the user. For example, simple or advanced graphing and plotting techniques may be applied in a similar manner as illustrated with respect to FIGS. 6-9. Alternatively, color-coding and other visualization techniques may also be used as illustrated in FIG. 10.

Figure 10:
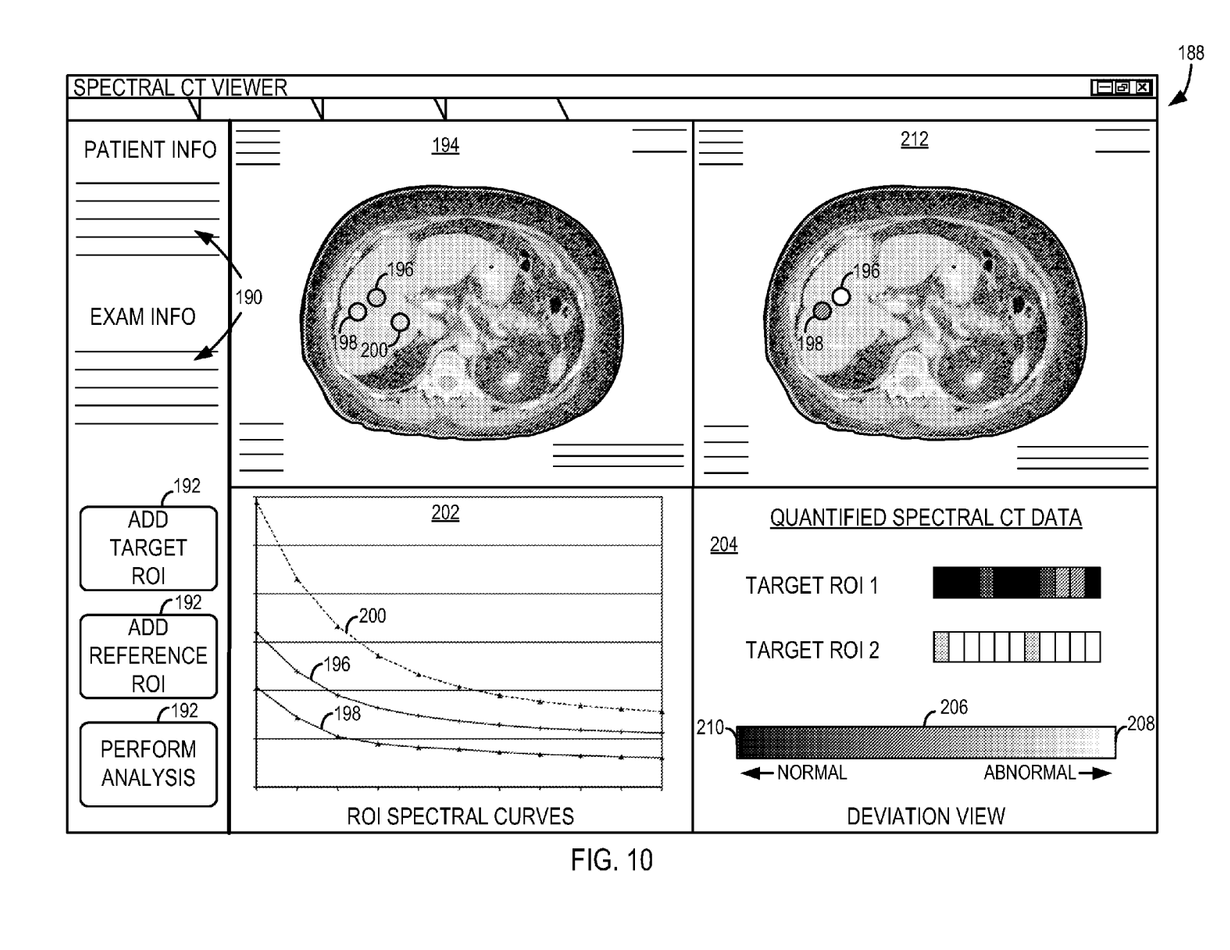
FIG. 10 is an exemplary user interface that includes a visual representation of deviation of a number of regions of interest in accordance with an embodiment of the present invention.

FIG. 10 illustrates an exemplary graphical user interface (GUI) 188 that may be used to display visual representations of ROIs, such as ROIs selected at steps 76, 80 (FIG. 5), visual representations of spectral curves, such as HU curves computed at steps 78, 82 or normalized curves of steps 110, 112 (FIG. 5), and visual representations of deviation metrics, such as metrics extracted at step 142 or metrics calculated at step 184 (FIG. 5).

GUI 188 includes a region 190 for displaying numeric and textual data, according to various embodiments, including patient image data, reference image data, patient-specific data, reference-specific data, and exam data, as examples. Optionally, region 190 may be configured as a control panel to permit a user to input and/or select data through input fields, dropdown menus, etc. GUI 188 also includes a number of user-selectable buttons 192 to facilitate user interaction with GUI 188. As shown, buttons 192 may provide functionality for adding a target ROI, reference ROI, or initiating analysis, as examples.

GUI 188 includes a first image region 194 that displays patient image data, allowing a user to select any number of target ROIs 196, 198 and any number of reference ROIs 200 in the image region 194. In one embodiment, reference ROI 200 is selected to correspond to normal tissue. ROIs 196-200 alternatively may be selected by an automated algorithm and displayed to a user in region 194.

GUI 188 also includes a region 202 for visualizing plots of spectral curves, such as plot 84 (FIG. 6) or plot 114 (FIG. 7), and/or plots of metrics, such as plot 144 (FIG. 8) or plot 176 (FIG. 9). While region 202 is shown as displaying a single plot, region 202 may also be configured to simultaneously display multiple plots. GUI 188 also includes a region 204 for displaying quantified spectra CT data for the selected target ROIs. A common color scale 206 is provided to normalize the quantified spectral CT data for the target ROIs so that the deviation may be compared across target ROIs. Thus, a TROI having spectral CT data that deviates greatly from the RROI is coded to correlate to a first end 208 of color scale 206 while a TROI with spectral CT data that closely correlates to the RROI is displayed to correspond to a second end 210 of color scale 206, opposite first end 208.

GUI 188 includes a second image region 212 that displays target ROIs 196, 198 color-coded to correspond to color scale 206, thereby allowing a user to quickly and easily visualize the deviation of TROIs 196, 198. It is noted that the arrangement of GUI 188 is provided merely for explanatory purposes, and that other GUI arrangements, field names, and visual outputs may take different forms. Additional display techniques may also include temperature gauges, graphs, dials, font variations, annotations, and the like.

Figure 11:
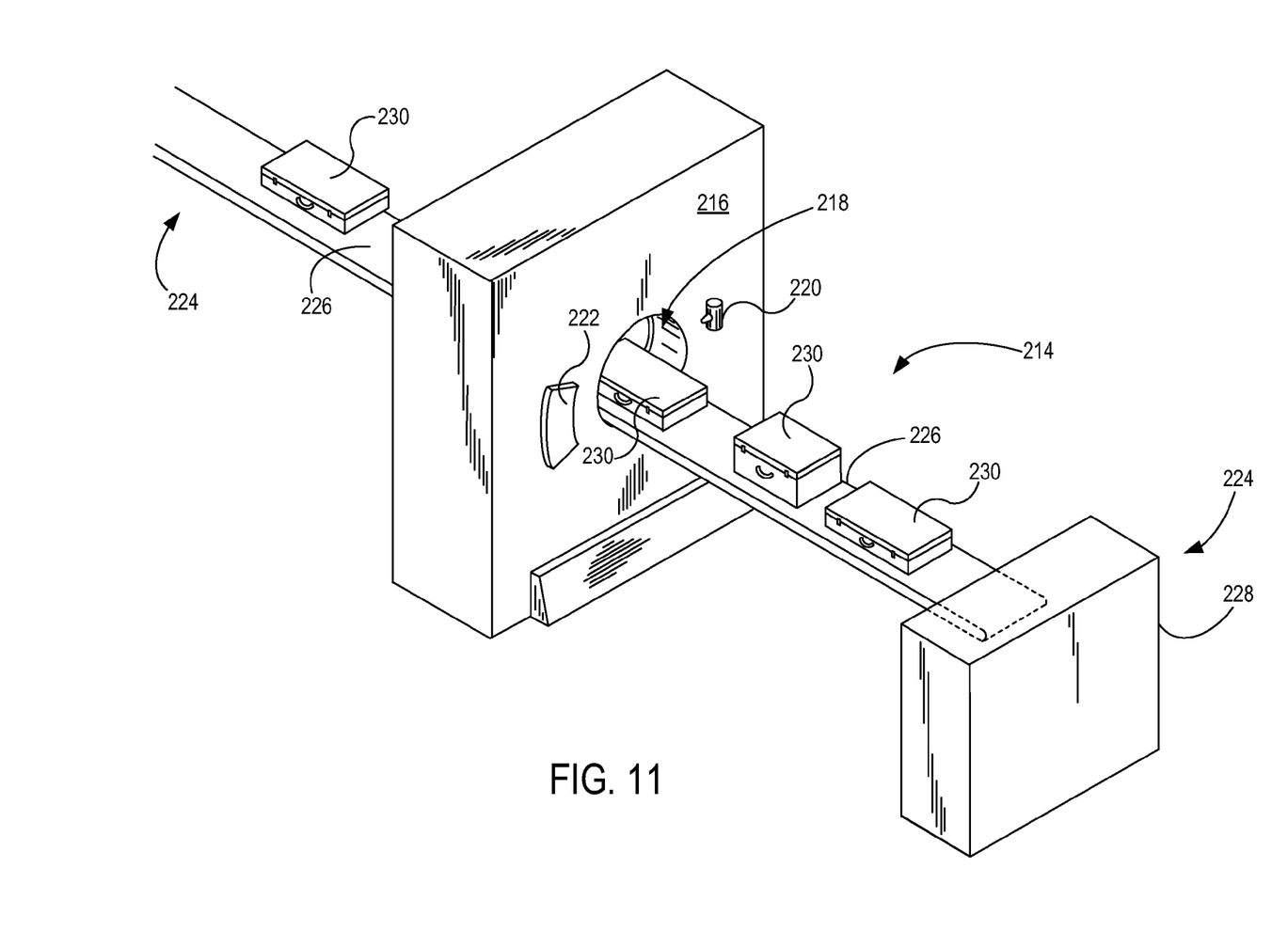
FIG. 11 is a pictorial view of a CT system for use with a non-invasive package inspection system.

Referring now to FIG. 11, package/baggage inspection system 214 includes a rotatable gantry 216 having an opening 218 therein through which packages or pieces of baggage may pass. The rotatable gantry 216 houses a high frequency electromagnetic energy source 220 as well as a detector assembly 222 having scintillator arrays comprised of scintillator cells similar to that shown in FIG. 3 or 4. A conveyor system 224 is also provided and includes a conveyor belt 226 supported by structure 228 to automatically and continuously pass packages or baggage pieces 230 through opening 218 to be scanned. Objects 230 are fed through opening 218 by conveyor belt 226, imaging data is then acquired, and the conveyor belt 226 removes the packages 230 from opening 218 in a controlled and continuous manner. As a result, postal inspectors, baggage handlers, and other security personnel may non-invasively inspect the contents of packages 230 for explosives, knives, guns, contraband, etc.

A technical contribution for the disclosed method and apparatus is that is provides for a computer implemented system and method of analyzing and visualizing spectral CT data.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, in accordance with one embodiment, a non-transitory computer readable medium has stored thereon a computer program comprising instructions, which, when executed by a computer, cause the computer to access a set of image data acquired from a patient, the set of image data comprising spectral CT data. The instructions also cause the computer to identify a plurality of TROIs from the set of image data, identify a RROI from the set of image data, and extract a plurality of target spectral HU curves from image data representing the plurality of TROIs. Further, instructions cause the computer to extract a reference spectral HU curve from image data representing the RROI, normalize the plurality of target spectral HU curves with respect to the reference spectral HU curve, and display the plurality of normalized target spectral HU curves.

In accordance with another embodiment, a method includes accessing an image dataset comprising spectral CT data acquired from a patient, creating a plurality of TROIs from the image dataset, and extracting a target dataset from the image dataset, the target dataset comprising image data corresponding to the TROIs. The method also includes computing a plurality of target spectral curves from the target dataset, each target spectral curve representing x-ray attenuation for a respective TROI, creating a RROI from the image dataset, and extracting a reference dataset from the image dataset, the reference dataset comprising image data corresponding to the RROI. Further, the method includes computing a reference spectral curve from the reference dataset, normalizing the plurality of target spectral curves with the reference spectral curve, and outputting a visualization of the plurality of normalized target spectral curves.

In accordance with yet another embodiment, a system for analyzing image data includes a database having stored thereon a patient image dataset acquired from a patient that includes spectral CT data. The system also includes a processor that is programmed to access the image dataset, identify a plurality of TROIs from the patient image dataset, and identify at least one RROI from the patient image dataset. The processor is also programmed to extract spectral CT data for the plurality of TROIs and the RROI from the patient image dataset, generate a plurality of target curves for the plurality of TROIs from the extracted spectral CT data, and generate at least one reference curve for the at least one RROI from the extracted spectral CT data. Further, the processor is programmed to normalize the plurality of target curves with the at least one reference curve, and output the plurality of normalized target curves. The system also includes a GUI configured to display the plurality of normalized target curves to a user.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer readable medium having stored thereon a computer program comprising instructions, which, when executed by a computer, cause the computer to:
    access a set of image data acquired from a patient, the set of image data comprising spectral computed tomography (CT) data;
    identify a plurality of target regions of interest (TROIs) in the patient from the set of image data;
    identify a reference region of interest (RROI) in the patient from the set of image data;
    extract a plurality of target spectral Hounsfield unit (HU) curves from image data representing the plurality of TROIs;
    extract a reference spectral HU curve from image data representing the RROI;
    normalize the plurality of target spectral HU curves with respect to the reference spectral HU curve; and display the plurality of normalized target spectral HU curves.

2. The computer readable medium of claim 1 wherein the instructions further cause the computer to calculate a plurality of metrics from the normalized target spectral HU curves to represent the plurality of TROIs.

3. The computer readable medium of claim 2 wherein the instructions cause the computer to calculate an average HU value for each of the plurality of normalized target spectral HU curves.

4. The computer readable medium of claim 2 wherein the instructions that cause the computer to calculate the plurality of metrics from HU at a plurality of discrete keV levels of the normalized target spectral HU curves.

5. The computer readable medium of claim 2 wherein the instructions further cause the computer to apply a threshold to the plurality of metrics, wherein the threshold distinguishes a first type of anatomy from a second type of anatomy.

6. The computer readable medium of claim 5 wherein the instructions further cause the computer to define a confidence interval near the threshold to aid in distinguishing TROIs corresponding to the first type of anatomy from TROIs corresponding to the second type of anatomy.

7. The computer readable medium of claim 2 wherein the instructions further cause the computer to output a visualization of the plurality of metrics.

8. The computer readable medium of claim 1 wherein the instructions further cause the computer to:
 access a comparison database comprising pre-computed image data acquired from a reference population;
 identify a set of reference spectral CT data from the comparison database, the set of reference spectral CT data representing expected spectral CT data for at least one tissue type;
 compare the plurality of normalized target spectral HU curves to the set of reference spectral CT data; and
 generate a plurality of deviation metrics from the plurality of normalized target spectral HU curves, the plurality of deviation metrics representing deviation of the plurality of TROIs with respect to the set of reference spectral CT data.

9. The computer readable medium of claim 1 wherein the instructions further cause the computer to:
 apply a threshold to the plurality of normalized target spectral HU curves;
 generate an upper set of TROIs to include TROIs of the plurality of TROIs having normalized target spectral HU curves that are above the threshold;
 generate a lower set of TROIs to include TROIs of the plurality of TROIs having normalized target spectral HU curves that are below the threshold;
 identify the upper set of TROIs as a first type of tissue; and
 identify the second set of TROIs as a second type of tissue.

10. A method comprising:
 accessing an image dataset comprising spectral computed tomography (CT) data acquired from a patient;
 creating a plurality of target regions of interest (TROIs) in the patient from the image dataset via selection of anatomical locations or features;
 extracting a target dataset from the image dataset, the target dataset comprising image data corresponding to the TROIs;
 computing a plurality of target spectral curves from the target dataset, each target spectral curve representing x-ray attenuation for a respective TROI;
 creating a reference region of interest (RROI) in the patient from the image dataset via selection of an anatomical location or feature;
 extracting a reference dataset from the image dataset, the reference dataset comprising image data corresponding to the RROI;
 computing a reference spectral curve from the reference dataset;
 normalizing the plurality of target spectral curves with the reference spectral curve; and
 outputting a visualization of the plurality of normalized target spectral curves.

11. The method of claim 10 further comprising extracting a plurality of metrics from the plurality of normalized target spectral curves, each metric corresponding to a respective normalized target spectral curve.

12. The method of claim 11 further comprising:
 selecting a threshold to distinguish a first type of anatomy from a second type of anatomy; and
 applying the threshold to the plurality of metrics.

13. The method of claim 12 further comprising defining a confidence interval near the threshold to aid in distinguishing TROIs corresponding to the first type of anatomy from TROIs corresponding to the second type of anatomy.

14. The method of claim 10 wherein computing the reference spectral curve and the plurality of target spectral curves comprises calculating Hounsfield Unit data at a plurality of energy levels.

15. The method of claim 14 wherein computing the plurality of target spectral curves comprises calculating a mean intensity within each TROI; and
 wherein computing the reference spectral curve comprises calculating a mean intensity within the RROI.

16. The method of claim 10 wherein identifying the plurality of TROIs comprises identifying abnormal anatomy; and
 wherein identifying the RROI comprises identifying normal anatomy.

17. The method of claim 10 further comprising:
 accessing a pre-computed reference database having stored thereon spectral CT data acquired from a reference population;
 identifying at least one reference metric from the pre-computed reference database, the at least one reference metric representing an expected spectral characteristic of the TROIs;
 comparing the at least one reference metric to at least one of the plurality of metrics;
 calculating a deviation metric based on the comparison; and
 outputting a visualization of the deviation metric.

18. The method of claim 10 further comprising automatically creating at least one of the TROIs and RROI using an automated computer-based algorithm.

19. A system for analyzing image data comprising:
 a database having stored thereon a patient image dataset acquired from a patient, the patient image dataset comprising spectral computed tomography (CT) data;
 a processor programmed to:
  access the image dataset;
  identify a plurality of target regions of interest (TROIs) from the patient image dataset, the plurality of TROIs being at identified anatomical locations or features in the patient;

identify at least one reference region of interest (RROI) from the patient image dataset, the at least on RROI being at one or more identified anatomical locations or features in the patient;

extract spectral CT data for the plurality of TROIs and the RROI from the patient image dataset;

generate a plurality of target curves for the plurality of TROIs from the extracted spectral CT data;

generate at least one reference curve for the at least one RROI from the extracted spectral CT data;

normalize the plurality of target curves with the at least one reference curve; and output the plurality of normalized target curves; and a graphical user interface (GUI) configured to display the plurality of normalized target curves to a user.

20. The system of claim 19 wherein the processor is further programmed to extract at least one metric from at least one of the plurality of normalized target curves, the at least one metric corresponding to a respective normalized target curve; and wherein the GUI is further configured to display the at least one metric to the user.

21. The system of claim 20 wherein the processor is programmed calculate an average HU value at a plurality of discrete keV levels for the at least one of the plurality of normalized target curves.

22. The system of claim 20 wherein the processor is further programmed to apply a threshold to the at least one metric, wherein the threshold distinguishes a first type of anatomy from a second type of anatomy.

23. The system of claim 22 wherein the processor is further programmed to define a confidence interval near the threshold to aid in distinguishing TROIs corresponding to the first type of anatomy from TROIs corresponding to the second type of anatomy.

24. The system of claim 19 wherein the processor is further programmed to apply a threshold to the plurality of normalized target curves; and wherein the GUI is further configured to display the threshold plurality of normalized target curves to the user.

25. The system of claim 19 further comprising a reference database having stored thereon comparison spectral CT data acquired from a reference population, the comparison spectral CT data representing known spectral CT behavior for at least one type of healthy tissue; and wherein the processor is further programmed to:
  access the comparison spectral CT data;
  compare the spectral CT data for the plurality of TROIs with the comparison spectral CT data;
  generate a plurality of deviation metrics based on the comparison, the plurality of deviation metrics representing deviation of respective TROIs with respect to the comparison spectral CT data; and
  output a visualization of the plurality of deviation metrics for the TROIs.

26. The system of claim 25 wherein the GUI is further configured to:
  display the plurality of TROIs on a common image; and
  color-code the plurality of TROIs based on plurality of deviation metrics.

\* \* \* \* \*